US00PP25605P3

(12) United States Plant Patent
Egger

(10) Patent No.: US PP25,605 P3
(45) Date of Patent: May 26, 2015

(54) ***HEUCHERA* PLANT NAMED 'MIDNIGHT RUFFLES'**

(50) Latin Name: ***Heuchera* hybrid**
Varietal Denomination: Midnight Ruffles

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 172 days.

(21) Appl. No.: 13/986,946

(22) Filed: Jun. 18, 2013

(65) Prior Publication Data

US 2014/0373237 P1 Dec. 18, 2014

(51) Int. Cl.
*A01H 5/02* (2006.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant substantially as shown and described, characterized by large, shiny, red brown to purple brown to almost black leaves, very cut and ruffled leaves showing red purple backs, a medium large plant size, small purple-brown flowers in spring, and good vigor.

2 Drawing Sheets

Botanical denomination: *Heuchera* hybrid.
Variety designation: 'Midnight Ruffles'.

BACKGROUND OF THE INVENTION

The present invention relates to a new and distinct cultivar of *Heuchera* and given the cultivar name of 'Midnight Ruffles'. *Heuchera* is in the family Saxifragaceae. *Heuchera* 'Midnight Ruffles' originated from a planned cross between *Heuchera* K580-8 (a proprietary unreleased plant)) as the seed parent, and *Heuchera* 148-1 (a proprietary unreleased plant) as the pollen parent. Compared to the seed parent, *Heuchera* K580-8, the new cultivar has larger leaves that are black rather than blue green and insignificant flowers rather than white flowers. Compared to the pollen parent, *Heuchera* 148-1, the new cultivar has leaves that are larger, black rather than amber colored, and more ruffled.

Compared to *Heuchera* 'Black Beauty' (U.S. Plant Pat. No. 13,288), the new cultivar has a much larger leaves and habit and leaves that are more ruffled.

Compared to *Heuchera* 'Chocolate Ruffles' (U.S. Plant Pat. No. 8,965), the new cultivar has larger, darker leaves.

Compared to *Heuchera* 'Black Taffeta' (U.S. Plant patent application Ser. No. 13/987,220), the new cultivar has longer leaves that are ovate rather than orbicular, with more of a purple tint, less glossy, more lobed, and has smaller, less showy flowers.

Compared to *Heuchera* 'Zipper', U.S. Plant patent application Ser. No. 13/987,219, the new cultivar has a larger habit and shinier foliage that is red brown to purple brown to almost black in color rather than golden amber to orange.

This new *Heuchera* is distinguished by:

1. large, shiny, red brown to purple brown to almost black leaves,
2. very cut and ruffled leaves showing red purple backs,
3. a medium large plant size, 4. small purple-brown flowers in spring, and
5. excellent vigor.

This new cultivar has been reproduced only by asexual propagation (cuttings and tissue culture). Each of the progeny exhibits identical characteristics to the original plant. Asexual propagation by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the flowers on an 18 month-old *Heuchera* 'Midnight Ruffles' growing in full sun May in Canby, Oreg.

FIG. 2 shows an 8 month-old *Heuchera* 'Midnight Ruffles' growing in full sun in the trial bed in November in Canby, Oreg.

FIG. 3 shows the summer foliage color of the new cultivar.

FIG. 4 shows the fall foliage color of the new cultivar on a 10 month old plant growing in full sun in the trial field in Canby, Oreg.

DETAILED PLANT DESCRIPTION

The following is a detailed description of the new *Heuchera* cultivar based on observations of two year-old specimens grown in the ground in the trial bed in shade in May in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 5th edition, 2007.

Plant:

*Form*.—Basal rosette, herbaceous perennial.

*Hardiness*.—USDA Zone 4 to 9.

*Size*.—33 cm tall from top of the foliage to the ground and 63 cm wide.

*Habit*.—Mounding.

*Vigor*.—Excellent.

*Roots*.—Fibrous, freely branching, fine, and white in color; roots develop easily from stem cuttings.

Leaf:

*Type*.—Simple.

*Arrangement*.—Basal.

*Shape*.—Broadly ovate.

*Lobing/division*.—5 main lobes, with 3 to 5 shallow secondary lobes, secondary lobes also lobed.

*Venation*.—Palmate.

*Margins*.—Crenate, undulate and ruffled.

*Apex*.—Mucronulate.

*Base*.—Cordate, lobes overlapping at the base.

*Blade size*.—Grows to 15 cm long and 12 cm wide.

*Surface texture*.—Both sides glandular puberulent.

*Petiole description*.—Grows to 21.5 cm long and 5 mm wide, pubescent, closest to Greyed Purple 187C.

*Leaf color*.—Variable depending on the time of the year, the temperature, and the exposure; winter and spring topside closest to Greyed Purple 186B with veins 187A, bottom side Purple N79A; summer topside between Brown 200B and Greyed Purple 183A, bottom side Purple N79A; fall topside Greyed Purple 183A, bottom side Purple N79A.

Inflorescence:

*Size*.—Grows to 6 cm wide and 31 cm long.

*Type*.—Thyrse.

*Number of flowers per thyrse*.—90 to 120 per thyrse.

*Number of thyrse*.—About 10.

*Peduncle*.—Grows to 36 cm tall, 5 mm wide at base, Purple N77A, glandular hairs, with 1 to 2 petiolate leaves (ovate, blades grow to 4.5 cm long and 3.8 cm wide, 5 lobed, margin crenate, topside Greyed Purple N186B, bottom side Purple N79A; petioles to 5.5 cm long, glandular puberulent, Greyed Orange 165A).

*Pedicel*.—1 mm to 4 mm long, with glandular hairs, Yellow Green 145D in shade and Greyed Red 181B in sun.

*Bloom period*.—May in Canby, Oreg.

Flower bud:

*Size*.—2.5 mm wide and 4 mm long.

*Description*.—Glandular puberulent, ovoid.

*Color*.—Greyed Purple 187B on bottom ¾ blending to Yellow Green 145C on top ¼.

Flower:

*Type*.—Perfect.

*Shape*.—Campanulate.

*Size*.—6 mm long and 5 mm to 6 mm wide.

*Petal description*.—5 in number, 4 mm long and less than 1 mm wide, reflexed, spatulate with a clawed base, tip acute, margin entire, glabrous on top and sparsely glandular puberulent on bottom, White NN155C on both sides.

*Calyx description*.—4 mm long and 4 mm wide, with 5 lobes, widely spaced, divided ½ way to the base, glandular hairs on outside, glabrous inside, tip acute, margin entire, outside Greyed Purple 187B on bottom ¾ blending to Yellow Green 145C on top ¼ (more where shaded), inside Yellow Green 145C.

*Stamen description*.—5 in number, each 4 mm long, filaments 3 mm long, White NN155C, anthers Yellow Orange 22A, no pollen, male sterile.

*Pistil description*.—One central two beaked pistil, 6 mm long, Yellow Green 145C overall, ovary 2 mm long.

*Fragrance*.—None.

*Lastingness*.—Each thyrse blooms for about 2 weeks on the plant.

Fruit:

*Type*.—Two-beaked ovoid capsule.

*Fertility*.—Low.

*Color*.—Greyed Brown 199C.

Seed:

*Shape*.—Linear.

*Size*.—2 mm long.

*Color*.—Black 202A.

Disease and pest tolerance: Pest and disease resistance are typical for this type of *Heuchera*. No known resistances.

I claim:

1. A new and distinct *Heuchera* plant as herein illustrated and described.

* * * * *

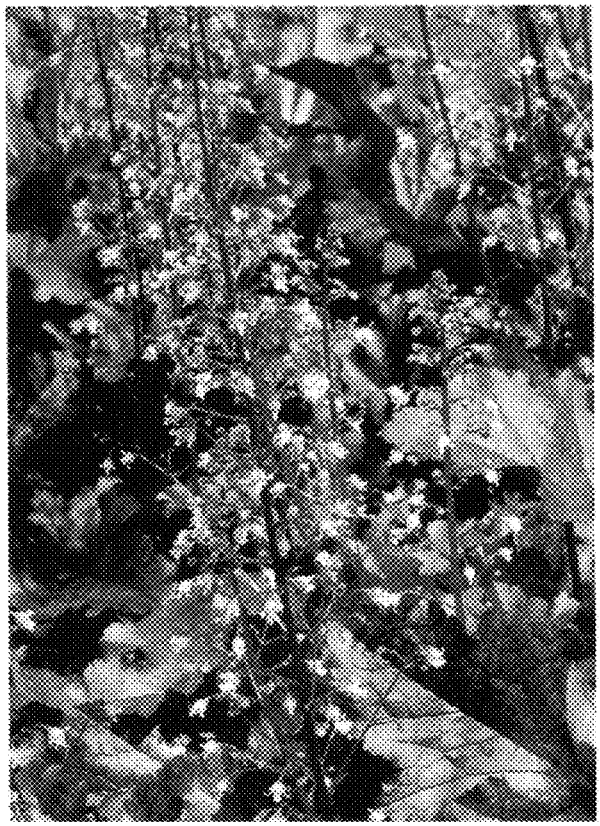
FIG. 1 on left,
FIG. 2 below
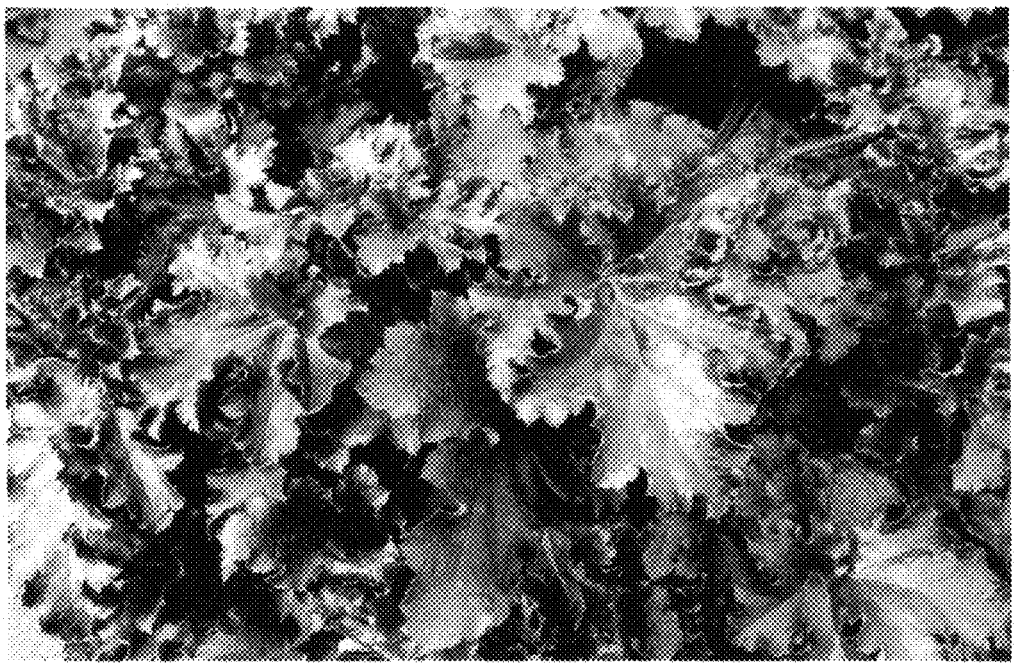

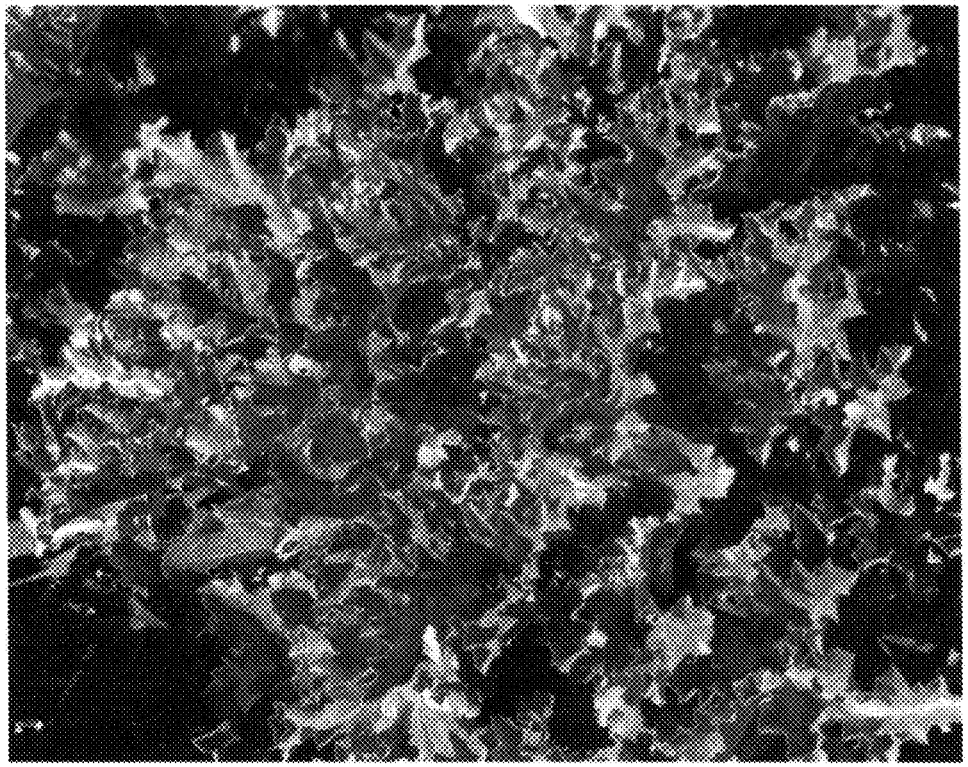

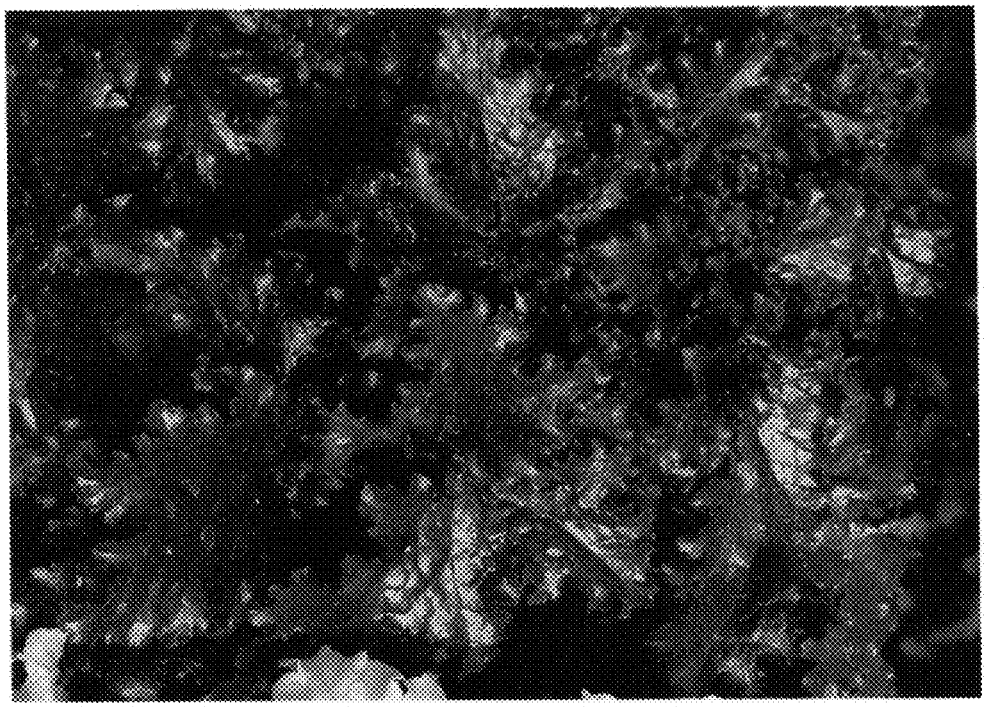
FIG. 3 above, FIG. 4 below